(12) United States Patent
Healy et al.

(10) Patent No.: US 8,024,964 B2
(45) Date of Patent: Sep. 27, 2011

(54) METHOD AND SYSTEM TO DETERMINE COMPOSITION OF FUEL ENTERING COMBUSTOR

(75) Inventors: Timothy Andrew Healy, Simpsonville, SC (US); John Charles Intile, Simpsonville, SC (US); Joseph Vincent Citeno, Greenville, SC (US); Garth Curtis Frederick, Greenville, SC (US)

(73) Assignee: General Electric Company, Schenectady, NY (US)

( * ) Notice: Subject to any disclaimer, the term of this patent is extended or adjusted under 35 U.S.C. 154(b) by 113 days.

(21) Appl. No.: 12/569,507

(22) Filed: Sep. 29, 2009

(65) Prior Publication Data

US 2010/0011851 A1 Jan. 21, 2010

Related U.S. Application Data

(62) Division of application No. 11/850,799, filed on Sep. 6, 2007, now Pat. No. 7,628,062.

(51) Int. Cl.
*G01M 15/14* (2006.01)

(52) U.S. Cl. ...................................... 73/112.03

(58) Field of Classification Search ............... 73/112.01, 73/112.03, 114.55, 112.04
See application file for complete search history.

(56) References Cited

U.S. PATENT DOCUMENTS

| | | | |
|---|---|---|---|
| 6,782,317 B2 | 8/2004 | Mitchell et al. | |
| 2003/0056578 A1 | 3/2003 | Mitchell et al. | |
| 2003/0094000 A1 | 5/2003 | Zagranski et al. | |
| 2007/0101724 A1 | 5/2007 | Gadde et al. | |
| 2007/0119178 A1 | 5/2007 | Berenbrink et al. | |

*Primary Examiner* — Eric S McCall
(74) *Attorney, Agent, or Firm* — Cantor Colburn LLP

(57) ABSTRACT

Disclosed is a method and system for determining composition of a fuel entering a combustor. The method includes determining a temperature of the fuel entering the combustor, calculating a first estimated total fuel flow utilizing fuel properties and fuel nozzle effective area ($A_e$), and calculating a second estimated total fuel flow utilizing an aero-thermal cycle model analysis. The first estimated total fuel flow is compared to the second estimated total fuel flow and a lower heating value of the fuel is determined from a difference between the first estimated total fuel flow and the second estimated total fuel flow. A method and system for controlling a gas turbine includes calculating effects of the fuel composition on performance of the gas turbine and comparing one or more performance parameters to one or more parameter limits. One or more machine controls of the gas turbine are changed based on the results of the comparison.

9 Claims, 2 Drawing Sheets

METHOD AND SYSTEM TO DETERMINE COMPOSITION OF FUEL ENTERING COMBUSTOR

CROSS REFERENCE TO RELATED APPLICATION

This is a divisional application related to U.S. application Ser. No. 11/850,799 filed Sep. 6, 2007 entitled, "METHOD AND SYSTEM TO DETERMINE COMPOSITION OF FUEL ENTERING COMBUSTOR."

BACKGROUND

The subject invention relates to gas turbines. More particularly, the subject invention relates to the identification and integration of fuel composition information into the cycle and combustion models used to control the gas turbine.

Performance of gas turbines is sensitive to the composition of the fuel feeding the gas turbine combustion system. Uncompensated variation in fuel composition can lead to combustion instabilities (dynamics), increased emissions including $NO_x$ and CO, lean blow-out, and reduced flame-holding margin or flashback. Timely understanding of varying fuel composition can aid optimization of the combustion system by the gas turbine control system. One method of accomplishing compensation for varying fuel composition includes direct measurement of fuel composition that can be accomplished by a variety of technologies, many of which are costly, slow in response, or otherwise undesirable for control purposes.

BRIEF DESCRIPTION OF THE INVENTION

The present invention solves the aforementioned problems by providing a method and system for determining composition of a fuel entering a combustor. The method includes determining a temperature and pressure of the fuel entering the combustor, calculating a first estimated total fuel flow utilizing fuel properties and fuel nozzle effective area ($A_e$), and calculating a second estimated total fuel flow utilizing an aero-thermal cycle model analysis. The first estimated total fuel flow is compared to the second estimated total fuel flow and a change in lower heating value of the fuel is inferred from a difference between the first estimated total fuel flow and the second estimated total fuel flow.

Further disclosed is a method and system for controlling a gas turbine includes calculating effects of the fuel composition on performance of the gas turbine and comparing one or more performance parameters to one or more parameter limits. One or more machine controls of the gas turbine are changed based on the results of the comparison.

These and other advantages and features will become more apparent from the following description taken in conjunction with the drawings.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Figure 1:
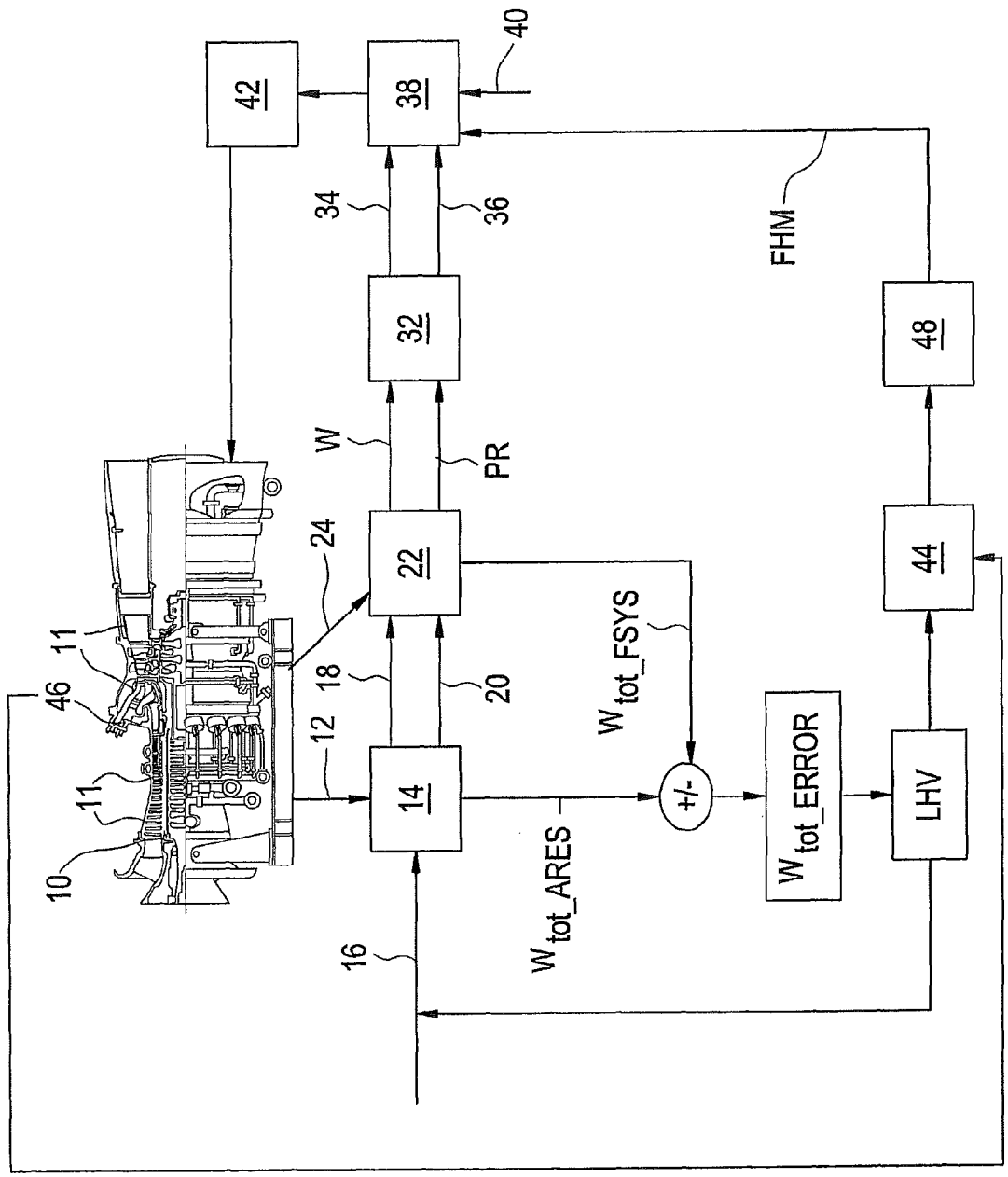
FIG. 1 is a schematic of a system for controlling a gas turbine.

Referring to FIG. 1, a gas turbine 10 includes a plurality of data sensors 11 distributed throughout the gas turbine 10. The data sensors 11 are shown here for illustrative purposes and may vary in quantity and/or location to provide the desired data. The data sensors 11 provide a range of data 12 from the gas turbine 10 such as, for example, temperatures, pressures, speeds, and generator output. The data 12 from the data sensors 11 is input into an aero-thermal cycle model 14 along with a baseline or assumed fuel composition 16. The aero-thermal cycle model 14 provides aero-thermal cycle model outputs 18 including, for example, combustion chamber pressure ($P_{CC}$), and fuel properties 20. The aero-thermal cycle model outputs 18, 20 are provided to a fuel system model 22.

Figure 2:
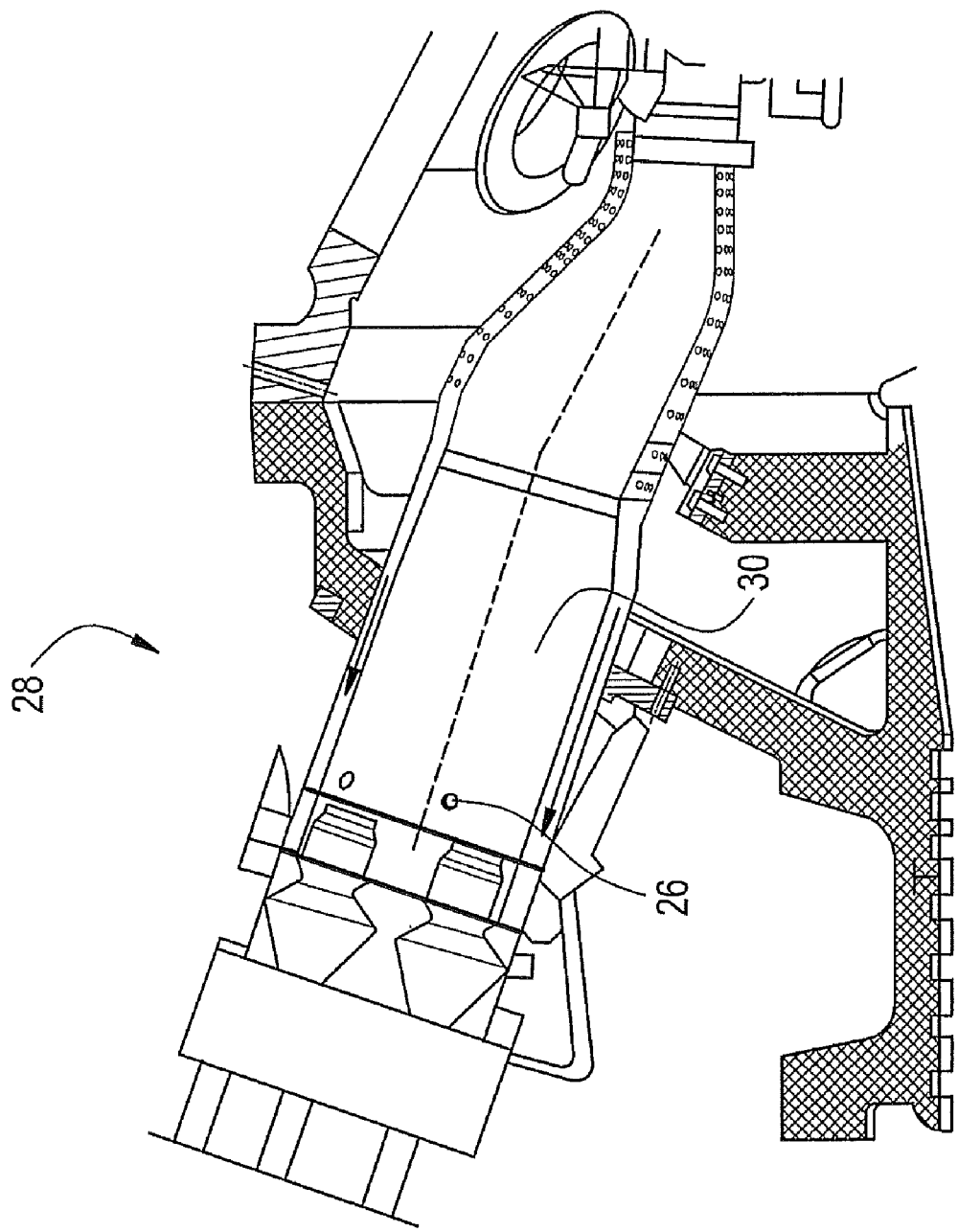
FIG. 2 is a cross-sectional view of a combustor of a gas turbine.

In some embodiments, an additional input to the fuel system model 22 is a fuel temperature 24. The fuel temperature 24 is preferably (but not necessarily) measured, as shown in FIG. 2, at one or more injector nozzles 26 of a combustor 28, to accurately measure the temperature of fuel entering a combustion chamber 30. Referring again to FIG. 1, once the fuel temperature 24 is determined, it is input into the fuel system model 22. The fuel system model 22 calculates a combustor pressure ratio (PR) which in conjunction with the fuel properties 20 and the fuel nozzle effective area ($A_e$) is utilized to calculate a total fuel flow ($W_{tot-FSYS}$) at the combustor 28. $W_{tot-FSYS}$ is compared to a total fuel flow calculated by the aero-thermal cycle model 14, $W_{tot-ARES}$, thus comparing the flow calculated based on actual fuel composition ($W_{tot-FSYS}$) to flow calculated based on the assumed fuel composition 16. The difference, $W_{tot-ERROR}$, between $W_{tot-FSYS}$ and $W_{tot-ARES}$, is indicative of a change in lower heating value (LHV) of the fuel in the combustor 28, which is a key identifier of fuel composition.

The LHV is input into the aero-thermal cycle model 14 as a new assumed fuel composition 16, new aero-thermal cycle model outputs 18 are input into the fuel system model 22, and a new $Wtot_{-FSYS}$ is output by the fuel system model 22. $W_{tot-FSYS}$ is again compared to $W_{tot-ARES}$ resulting in a new $W_{tot-ERROR}$ and a new LHV. This process of error reduction continues until $W_{tot-ERROR}$ equals zero.

Once error reduction is achieved, total flow W and pressure ratio PR are input to a first transfer function 32 which outputs data related to performance of the gas turbine 10, for example, emissions data 34 and dynamics data 36. The data 34, 36 is fed to a control function 38 which compares the data 34, 36 to value limits 40. If the data 34, 36 exceeds one or more of the limits 40, the control function 38 may cause a change to one or more machine controls 42 to change operating parameters of the gas turbine 10, such as inlet guide vane angle and/or nozzle area. This method allows control of the gas turbine 10 which is sensitive to changes in the fuel composition, and has the ability to quickly adjust the machine controls 42 in reaction to changes in the fuel composition.

In some embodiments, the relative quantities of constituent elements in the fuel are determined. This determination is especially useful in evaluating a flameholding margin (FHM) of a particular fuel, and adjusting machine controls 40 in reaction to it. For example, in a gas turbine 10 where the fuel is a natural gas, it is advantageous to know the relative quantities of constituents methane, ethane, butane, and propane present in the fuel. In this embodiment, once the LHV is determined as described above, a relative constituent model 44 is utilized to estimate the relative quantities of the constituents present in the fuel.

In another embodiment, direct measurement of one or more constituents may be utilized to determine relative constituent content. One or more constituent sensors, for example, optical devices 46, tuned to detect a specific constituent may be placed in a fuel stream (not shown) of the gas turbine 10. The output from the one or more optical devices 46 is then directed to the relative constituent model 44, where the relative amounts of the remaining constituents are determined. The output from the one or more optical devices 46 is also utilized to tune the relative constituent model 44, thus improving confidence in future iterations.

Once the constituent amounts are determined as above, an FHM transfer function 48 is utilized to determine the FHM of the particular fuel composition. The FHM is then input into the control function 38 and compared to a limit 40. The control function 38 evaluates the FHM relative to the limit 40 and determines whether an adjustment to one or more of the machine controls 42 is necessary, and directs the change if it is necessary.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A method for controlling a gas turbine comprising:
   determining a temperature of the fuel entering the combustor of the gas turbine;
   determining composition of a fuel entering the combustor of the gas turbine via the temperature measurement;
   calculating effects of the fuel composition on performance of the gas turbine;
   comparing one or more performance parameters to one or more parameter limits; and
   changing one or more machine controls of the gas turbine based on the results of the comparison.

2. The method of claim 1 wherein the composition of a fuel is determined by:
   calculating a first estimated total fuel flow utilizing fuel properties and fuel nozzle effective area ($A_e$);
   calculating a second estimated total fuel flow utilizing an aero-thermal cycle model analysis;
   comparing the first estimated total fuel flow to the second estimated total fuel flow; and
   determining a lower heating value of the fuel from a difference between the first estimated total fuel flow and the second estimated total fuel flow.

3. The method of claim 2 including determining proportions of one or more constituents in the fuel.

4. The method of claim 3 wherein the proportions of one or more constituents are determined by inputting the lower heating value into a relative constituent model.

5. The method of claim 3 wherein the proportions of one or more constituents are determined by utilizing one or more constituent sensors to measure quantities of one or more constituents.

6. The method of claim 3 wherein the proportions of one or more constituents are determined by:
   utilizing one or more constituent sensors to determine a quantity of at least one constituent of the one or more constituents;
   inputting the quantity of the at least on constituent into a relative constituent model; and
   determining the relative quantities of remaining desired constituents by inputting the lower heating value into the relative constituent model.

7. The method of claim 3 including calculating a flameholding margin by utilizing proportions of one or more constituents in the fuel.

8. The method of claim 7 including:
   comparing the flameholding margin to a flameholding margin limit; and
   changing one or more machine controls of the gas turbine based on the results of the comparison.

9. The method of claim 1 wherein the temperature of the fuel entering the combustor is determined by measuring the temperature of the fuel at an exit of at least one injector nozzle in the combustor.

* * * * *